(12) United States Patent
Yuan et al.

(10) Patent No.: US 10,107,737 B2
(45) Date of Patent: Oct. 23, 2018

(54) APPARATUS AND METHOD FOR EVALUATING FILM ADHESION

(71) Applicants: BOE TECHNOLOGY GROUP CO., LTD., Beijing (CN); HEFEI BOE OPTOELECTRONICS TECHNOLOGY CO., LTD., Hefei, Anhui (CN)

(72) Inventors: Min Yuan, Beijing (CN); Hongwei Xing, Beijing (CN); Guilin Liu, Beijing (CN)

(73) Assignees: BOE TECHNOLOGY GROUP CO., LTD., Beijing (CN); HEFEI BOE OPTOELECTRONICS TECHNOLOGY CO., LTD., Hefei, Anhui (CN)

(*) Notice: Subject to any disclaimer, the term of this patent is extended or adjusted under 35 U.S.C. 154(b) by 456 days.

(21) Appl. No.: 14/751,516

(22) Filed: Jun. 26, 2015

(65) Prior Publication Data

US 2016/0282256 A1 Sep. 29, 2016

(30) Foreign Application Priority Data

Mar. 24, 2015 (CN) .......................... 2015 1 0130546

(51) Int. Cl.
G01B 3/44 (2006.01)
G01N 19/04 (2006.01)
G01N 3/08 (2006.01)

(52) U.S. Cl.
CPC .............. G01N 19/04 (2013.01); G01N 3/08 (2013.01)

(58) Field of Classification Search
CPC .......... G01N 19/04; G01N 19/00; G01N 3/08; G01N 3/00; G01N 3/30–3/307;
(Continued)

(56) References Cited

U.S. PATENT DOCUMENTS

| 5,477,732 A * | 12/1995 | Yasue | ................... | B82Y 35/00 |
|---|---|---|---|---|
| | | | | 257/E21.525 |
| 2011/0037687 A1* | 2/2011 | Akamatsu | ................ | G01N 3/24 |
| | | | | 345/87 |

(Continued)

FOREIGN PATENT DOCUMENTS

| CN | 88202086 | * 11/1988 | ............... G01N 3/04 |
|---|---|---|---|
| CN | 88202086 U | 11/1988 | |

(Continued)

OTHER PUBLICATIONS

First Chinese Office Action dated Oct. 27, 2016; Appln. No. 201510130546.3.

(Continued)

*Primary Examiner* — Eric Ward
*Assistant Examiner* — Eric Ashbahian
(74) *Attorney, Agent, or Firm* — Ladas & Parry LLP; Loren K. Thompson (57) ABSTRACT

An apparatus and a method for evaluating film adhesion are disclosed. The film is disposed on a first substrate, a side of the first substrate provided with the film is attached to a second substrate, and the film is divided into units. The apparatus includes an evaluation machine, which includes an upper fixing mechanism and a lower fixing mechanism disposed opposite to each other, the second substrate is detachably fixed on the upper fixing mechanism, and a side of the first substrate not provided with the film is detachably fixed on the lower fixing mechanism. The evaluation machine further includes a force application device, which is configured to apply an external force to the upper fixing mechanism and/or the lower fixing mechanism, so that the upper fixing mechanism and the lower fixing mechanism generate relative movement away from each other.

17 Claims, 5 Drawing Sheets

(58) Field of Classification Search
CPC ............... G01N 2203/0417–2203/0458; G01N 2203/0091; H01L 21/683–21/68714; H01L 21/301; H01L 21/12
See application file for complete search history.

(56) References Cited

U.S. PATENT DOCUMENTS

| | | | | |
|---|---|---|---|---|
| 2013/0205885 A1* | 8/2013 | Zhang | ................... | G01N 19/04 73/150 A |
| 2015/0029428 A1* | 1/2015 | Wang | ................... | G02B 5/201 349/42 |
| 2015/0059488 A1* | 3/2015 | Chang | ................... | G01N 19/04 73/794 |

FOREIGN PATENT DOCUMENTS

| | | | | | |
|---|---|---|---|---|---|
| CN | 201083675 | | * | 7/2008 | ............ G01N 19/04 |
| CN | 201083675 | Y | | 7/2008 | |
| CN | 101446544 | A | | 6/2009 | |
| CN | 102323209 | A | | 1/2012 | |
| CN | 202471571 | U | | 10/2012 | |
| CN | 102937571 | A | | 2/2013 | |
| CN | 202916180 | U | | 5/2013 | |
| CN | 203178172 | U | | 9/2013 | |
| CN | 203203915 | | * | 9/2013 | ............ G01N 19/04 |
| CN | 103364337 | A | | 10/2013 | |
| CN | 203456422 | U | | 2/2014 | |
| CN | 103940736 | A | | 7/2014 | |
| CN | 203849155 | U | | 9/2014 | |
| JP | 11118705 | A | | 4/1999 | |
| JP | 2007-163147 | A | | 6/2007 | |
| JP | 2013076579 | A | | 4/2013 | |
| KR | 20070118343 | | * | 12/2007 | ............ G01M 7/00 |

OTHER PUBLICATIONS

Second Chinese Office Action dated Mar. 9, 2017; Appln. No. 201510130546.3.
Chen Zhiliang: "21.2.6.3 Method of Adhesive Tape Modern Painting Technology Handbook", Chemical Industry Press, Published, Jan. 31, 2010, pp. 773-774.
The Third Chinese Office Action dated Oct. 13, 2017; Appln. 201510130546.3.

* cited by examiner

APPARATUS AND METHOD FOR EVALUATING FILM ADHESION

TECHNICAL FIELD

Embodiments of the disclosure relate to an apparatus and a method for evaluating film adhesion.

BACKGROUND

Currently, liquid crystal displays (LCDs) have become important tools in people's daily living and working, and the people tend to use liquid crystal display panels in more and more different environments. Under an environment having a normal temperature, a normal humidity and a normal pressure, a display panel usually does not suffers from any quality problem; however, in some harsh environments, a color filter layer in the display panel is prone to be stripped off, leading to abnormal gaps in a product, and generating undesirable bubbles in the product. In a severe case, a problem of fissure between a color filter substrate and an array substrate will even occur. Therefore, it is particularly important to correctly evaluate film adhesion (force).

However, no uniform standard is proposed for the methods for evaluating the film adhesion at present. A common method is a scotch tape testing method, which segments a sample by using a cross-cutter manually, and thus can neither ensure a constant force for segmenting the sample, nor ensure a uniform segmentation area of the sample and a consistent number of segmented units for different samples. After the segmenting process, the sample is adhered with an adhesive tape, and then data of the stripped film is determined. Since it is impossible to ensure the force segmenting the film constant, a change of the film adhesion cannot be evaluated by a precise value, nor can a degree of reliability of the film adhesion under the harsh environment can be effectively evaluated.

In addition, existing evaluation methods are conducted based on a finished product of a display unit, which not only cause waste of resources and materials, but also increase risk of undesirable batches of products, and thus belong to ex post evaluation, and are not conducive to improvement of product quality.

SUMMARY

According to an embodiment of the present disclosure, there is provided an apparatus for evaluating film adhesion. The film is disposed on a first substrate, a side of the first substrate provided with the film is attached to a second substrate, and the film is divided into a plurality of units. The apparatus comprises an evaluation machine, the evaluation machine includes an upper fixing mechanism and a lower fixing mechanism disposed opposite to each other, the second substrate is detachably fixed on the upper fixing mechanism, and a side of the first substrate not provided with the film is detachably fixed on the lower fixing mechanism. The evaluation machine further includes a force application device, the force application device being configured to be able to apply an external force to the upper fixing mechanism and/or the lower fixing mechanism, so that the upper fixing mechanism and the lower fixing mechanism generate therebetween relative movement away from each other.

For example, the force application device includes a pull-down mechanism, and the pull-down mechanism is disposed below the lower fixing mechanism so as to apply a pulling force to the lower fixing mechanism.

For example, the pull-down mechanism includes at least one balancing weight detachably disposed below the lower fixing mechanism.

For example, the upper fixing mechanism includes an upper vacuum suction plate, and the lower fixing mechanism includes a lower vacuum suction plate.

For example, the apparatus further comprises a segmentation machine; the segmentation machine includes a stage, a cutter head disposed above the stage, and a pressure controller configured for controlling cutting pressure of the cutter head, the stage is configured for placing the first substrate, the side of the first substrate provided with the film is disposed toward the cutter head, and the segmentation machine is configured for segmenting the film into a plurality of units.

For example, a side of the cutter head toward the stage is provided with a plurality of blades uniformly spaced, the cutter head is able to move relative to the stage, and the cutter head is able to rotate around an installation shaft for installing the cutter head.

For example, the evaluation machine is further provided with a timer, the timer is configured for setting time for the force application device to apply a pulling force.

For example, the side of the first substrate provided with the film is attached to the second substrate by transparent adhesive.

For example, the film is a color filter layer.

For example, the apparatus further comprises a calculating module, the calculating module is configured for: establishing a coordinate system, with a horizontal axis x of the coordinate system as the external force or time, and a vertical axis y as the number of units whose film is stripped; drawing a plurality of points with coordinate values of $(x_N, y_N)$ in the coordinate system, N being a positive integer; fitting to obtain an equation of x and y according to the above coordinate values: $y=kx+C$, where k is a slope, and C is a constant.

For example, the apparatus further comprises a determining module, the determining module being configured for determining whether a sample under test has a reliability risk or not, according to difference of k values obtained respectively under a normal condition and a reliability test condition.

According to an embodiment of the present disclosure, there is provided a method for evaluating film adhesion. The method comprises steps of taking a first test sample, the first test sample including a first substrate and a film disposed on the first substrate; segmenting the film into a plurality of units; attaching a side of the first substrate provided with the film to a second substrate; detachably fixing the second substrate on an upper fixing mechanism, and detachably fixing a side of the first substrate not provided with the film on a lower fixing mechanism; applying, by a force application device, an external force with a predetermined value to the upper fixing mechanism and/or the lower fixing mechanism, so that the upper fixing mechanism and the lower fixing mechanism generate therebetween relative movement away from each other; taking one of the external force and time as a variable, and the other as a constant, then counting the number of units whose film is stripped under conditions where the variable is of different values, to obtain a relationship between the number of the units whose film is stripped and the variable.

For example, the force application device includes a pull-down mechanism, the pull-down mechanism being disposed below the lower fixing mechanism, and the external force refers to a pulling force that the pull-down mechanism applies to the lower fixing mechanism.

For example, the obtaining a relationship between the number of the units whose film is stripped and the variable includes: establishing a coordinate system, with a horizontal axis x of the coordinate system as the variable, and a vertical axis y as the number of the units whose film is stripped, drawing a plurality of points with coordinate values of $(x_N, y_N)$ in the coordinate system, N being a positive integer; fitting to obtain an equation of the number of the units whose film is stripped and the variable according to the above coordinate values: $y=k_1x+C_1$, where $k_1$ is a slope, and $C_1$ is a constant.

For example, the method further comprises: taking a second test sample, the second test sample also including a third substrate and a second film disposed on the third substrate; segmenting the second film into a plurality of units; placing the second test sample, after the second film is segmented, in a reliability test condition for predetermined time; attaching a side of the third substrate provided with the second film to a fourth substrate; detachably fixing the fourth substrate on the upper fixing mechanism, and detachably fixing a side of the third substrate not provided with the second film on the lower fixing mechanism; applying, by the force application device, an external force with a predetermined value to the upper fixing mechanism and/or the lower fixing mechanism, so that the upper fixing mechanism and the lower fixing mechanism generate therebetween relative movement away from each other; taking one of the external force and time as a variable, and the other as a constant, then counting the number of units whose film is stripped under conditions where the variable is of different values, to obtain an equation of the number of the units whose film is stripped and the variable under the reliability test condition: $y=k_2x+C_2$, where $k_2$ is a slope, and $C_2$ is a constant; calculating a speed of change of the film adhesion before and after environmental change, according to a formula $\Delta=[(k_2-k_1)/k_1]*100\%$, and determining that the sample has no reliability risk, when $\Delta$ is less than or equal to a predetermined percentage.

For example, the reliability test condition includes one or more conditions of temperature greater than 120° C., humidity greater than 95%, and pressure greater than 0.1 MPa, and the predetermined time being greater than 12 hours.

For example, the apparatus further comprises a segmentation machine, the segmentation machine includes a stage, a cutter head disposed above the stage, and a pressure controller configured for controlling a cutting pressure of the cutter head, the stage is configured for placing the first substrate, the side of the first substrate provided with the film is disposed toward the cutter head, and the segmentation machine is configured for segmenting the film into a plurality of units. In the segmenting the film into a plurality of units, the cutter head is controlled by using the pressure controller to segment the film into a plurality of units with a constant pressure.

For example, with the time as a constant, and the pulling force as a variable, the number of units whose film is stripped under different pulling force conditions is counted, to obtain a relationship between the number of the units whose film is stripped and the pulling force.

For example, with the pulling force as a constant, and the time as a variable, the number of the units whose film is stripped under different time conditions is counted, to obtain a relationship between the number of the units whose film is stripped and the time.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

DESCRIPTION OF THE EMBODIMENTS

In order to make objects, technical details and advantages of the embodiments of the disclosure apparent, the technical solutions of the embodiment will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Figure 1A:
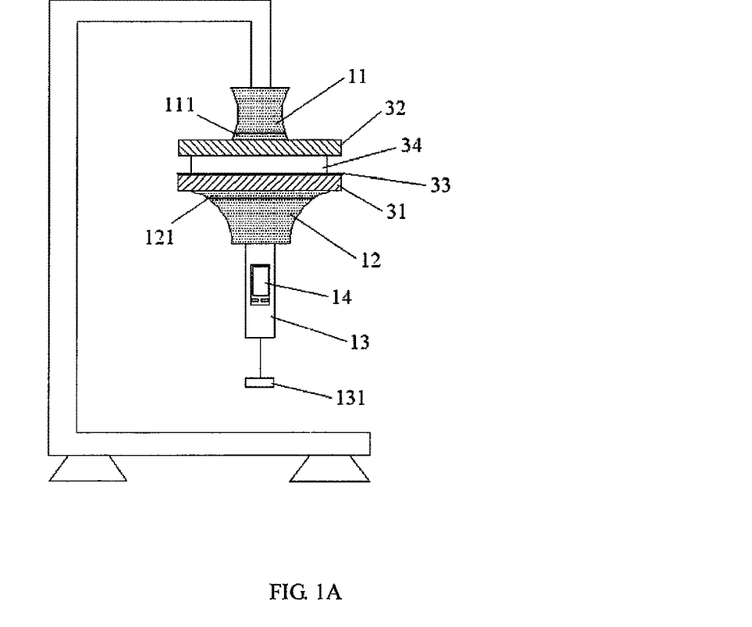
FIG. 1A is a structural schematic diagram of an evaluation machine according to an embodiment of the present disclosure.

An embodiment of the present disclosure provides an apparatus for evaluating film adhesion (force), the apparatus comprising an evaluation machine, and FIG. 1A is a structural schematic diagram of the evaluation machine according to the embodiment of the present disclosure. As shown in FIG. 1A, the evaluation machine includes an upper fixing mechanism 11 and a lower fixing mechanism 12 disposed opposite to each other, a film 33 is disposed on a first substrate 31, a side of the first substrate 31 provided with the film 33 is attached to a second substrate 32, and the film 33 is segmented into a plurality of units, for example, segmented into a plurality of units all with an equal size and an equal area. The second substrate 32 is detachably fixed on the upper fixing mechanism 11, and a side of the first substrate 31 not provided with the film 33 is detachably fixed on the lower fixing mechanism 12. The evaluation machine further includes a force application device, and the force application device is able to apply an external force to the upper fixing mechanism 11 and/or the lower fixing mechanism 12, so that the upper fixing mechanism 11 and the lower fixing mechanism 12 generate therebetween relative movement away from each other.

When the film adhesion is evaluated, one out of external force and time is taken as a variable, and the other as a constant, then the number of units, the film in which is striped under conditions where the variable is at different values, is counted, so that a relationship that the number of the units whose film is striped changes along with the external force or the time can be obtained.

The embodiment of the present disclosure can accurately obtain the rule that the film adhesion changes with the time or the external force. At the same time, the sample can be placed under a reliability test condition, to repeat the above-described evaluation process, and a change of the film adhesion before and after environmental change is analyzed by comparison, so as to evaluate whether an undesirable phenomenon will occur to a product in a reliability test or not.

For example, the film 33 is a color filter layer. In the related industry, the probability of occurrence of the undesirable phenomenon such as bubbles in a display unit in a reliability test is evaluated by analyzing an adhesion status of a color filter layer. In an embodiment of the present disclosure, it is only necessary to test a single product of a color filter substrate, which reduces waste of resources and materials, and can predict in advance and avoid a product quality risk.

In order that the upper fixing mechanism 11 and the lower fixing mechanism 12 can generate relative movement away from each other, an upward force can be applied to the upper fixing mechanism 11, or a downward force can be applied to the lower fixing mechanism 12, or these two types of forces as described above can be applied simultaneously.

For example, the force application device includes a pull-down mechanism 13, and the pull-down mechanism 13 is disposed below the lower fixing mechanism 12 so as to apply a downward pulling force to the lower fixing mechanism 12. In an embodiment of the present disclosure, the pull-down mechanism 13 includes at least one balancing weight 131 detachably disposed below the lower fixing mechanism 12. Since the weight of the balancing weight 131 can be predicted, the pulling force applied to the lower fixing mechanism 12 by the balancing weight 131 can also be predicted. Thus, as compared with a conventional technology, the embodiment of the present disclosure can ensure precise measurement of the force that is applied to strip the film, so the effect of evaluating the film adhesion is more reliable. In a case where the pull-down mechanism 13 is disposed, the pulling force can be provided by means of the weight of the pull-down mechanism 13 per se, which saves energy.

Specific structures of the upper fixing mechanism 11 and the lower fixing mechanism 12 will limit the embodiments of the present disclosure, as long as the first substrate 31 and the second substrate 32 can be detachably fixed thereon. For example, in order to facilitate control, the upper fixing mechanism 11 includes an upper vacuum suction plate 111, and the lower fixing mechanism 12 includes a lower vacuum suction plate 121. That is, the upper vacuum suction plate 111 in the upper fixing mechanism 11 is used for suctioning the second substrate 32, and the lower vacuum suction plate 121 in the lower fixing mechanism 12 is used for suctioning the side of the first substrate 31 not provided with the film 33.

For example, the evaluation machine is further provided with a timer 14, and the timer 14 can be used for setting the time period for the pull-down mechanism 13 to apply the pulling force. In a case where the time is at a constant value, the timer 14 enables a timing function, setting a predetermined time, then the pull-down mechanism 13 applies different pulling forces to the film 33 by adding the balancing weights 131 of different weights, and at the predetermined time, the upper vacuum suction plate in the upper fixing mechanism 11 and the lower vacuum suction plate in the lower fixing mechanism 12 stop suction suctioning, and stripping statuses of the film under different pulling forces are recorded/counted. In a case where the pulling force is at a constant value, the pull-down mechanism 13 applies a constant pulling force to the film 33 by adding the balancing weight 131 of a constant weight, and the timer 14 enables the timing function, and stripping statuses of the film in different periods of time are recorded/counted respectively.

For example, the side of the first substrate 31 provided with the film 33 is attached to the second substrate 32 by transparent adhesive 34, and the transparent adhesive 34 may be a kind of sealant. The second substrate 32, for example, is a transparent substrate, e.g., a transparent glass substrate or a transparent resin substrate, etc., in order to count the number of the units whose film is stripped under a microscope, after application of the pulling force is stopped.

Figure 1B:
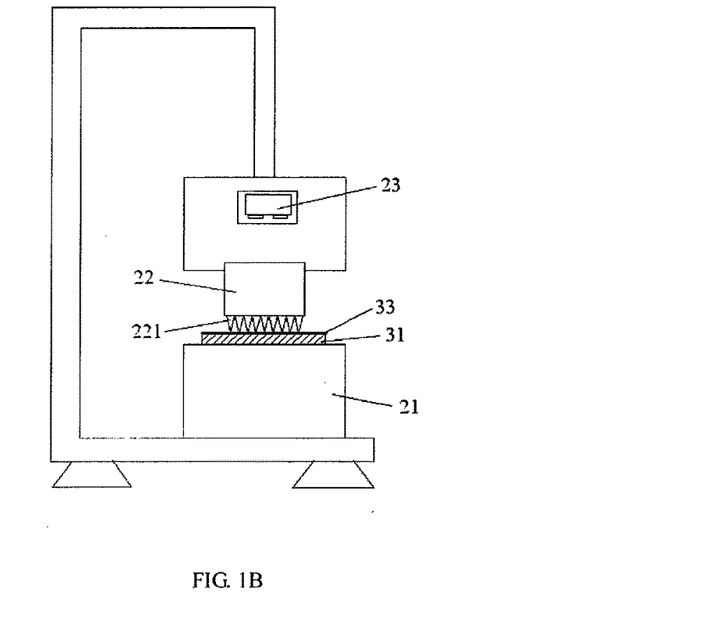
FIG. 1B is a structural schematic diagram of a segmentation machine according to the embodiment of the present disclosure.

For example, the apparatus further comprises a segmentation machine/equipment, and FIG. 1B is a structural schematic diagram of the segmentation machine according to an embodiment of the present disclosure. As shown in FIG. 1B, the segmentation machine includes a stage 21, a cutter head 22 disposed above the stage 21, and a pressure controller 23 for controlling a cutting pressure of the cutter head 22. The stage 21 is configured for placing the first substrate 31 thereon, the first substrate 31 is provided with the film 33, the side of the first substrate 31 provided with the film 33 is disposed toward the cutter head 22, and the segmentation machine is used for segmenting the film 33 into a plurality of units, and each unit may have an equal size.

The embodiment of the present disclosure, by providing the pressure controller 23 on the cutter head 22 so that the film 33 is divided into a plurality of units at a constant force, avoids an error caused by cutting manually in the conventional technology, and makes an analysis result more accurate and reliable.

For example, the side of the cutter head 22 facing the stage 21 is provided with a plurality of blades 221 uniformly spaced from one another, the cutter head 22 can be moved relative to the stage 21, and the cutter head 22 can rotate around an installation shaft for installing the cutter head 22. For example, the film 33 is divided into a plurality of units with an equal size and an equal area.

For example, the apparatus may further comprise a conveying mechanism, which conveys the first substrate 31 and the segmented film 33 from the segmentation machine to the evaluation machine. For example, the conveying mechanism is a conveyor belt.

Figure 2:
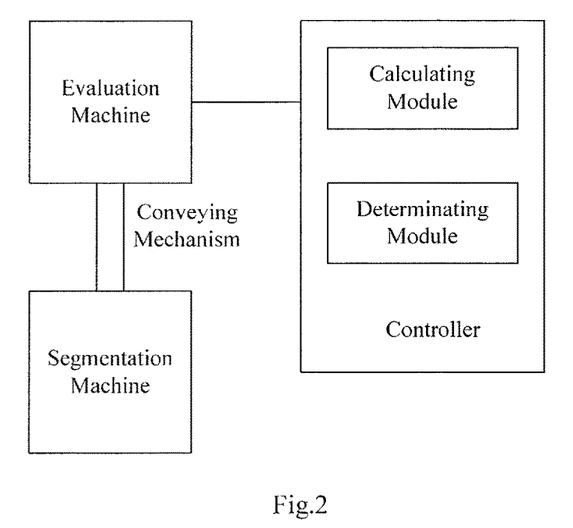
FIG. 2 is a block diagram of an equipment according to an embodiment of the present disclosure.

FIG. 2 is a block diagram of an equipment according to an embodiment of the present disclosure. As shown in FIG. 2, the equipment comprises an evaluation machine, a segmentation machine, a conveying mechanism between the evaluation machine and the segmentation machine, and a controller. The controller is connected to the evaluation machine for example, and may be connected to both the evaluation machine and the segmentation machine. The controller comprises modules/units for control, calculate, etc.

For example, the apparatus may further comprise a calculating module, the calculating module being configured for: establishing a coordinate system, with a horizontal axis x of the coordinate system as the external force or time and a vertical axis y as the number of units whose film is stripped; drawing/plotting a plurality of points with coordinate values of $(x_N, y_N)$ in the coordinate system, N being a positive integer; fitting to obtain an equation of x and y according to the above coordinate values: $y=kx+C$, where k is a slope, and C is a constant, so as to obtain the relationships that the film adhesion changes with time or external force.

For example, the apparatus may further comprise a determining module, the determining module is configured for determining whether a sample under a test has a reliability risk or not, according to a difference of k values obtained respectively under the normal condition and the reliability test condition. The calculating module and determining module may be embodied in hardware, firmware, or software, for example, as a central processing unit (CPU) or digital signal processor (DSP).

An embodiment of the present disclosure further provides a method for evaluating film adhesion by using the apparatus as described above. For example, the method comprises steps of: taking a first test sample, the first test sample including a first substrate and a film disposed on the first substrate; segmenting the film into a plurality of units, for example, segmenting the film into a plurality of units all with an equal size and an equal area; attaching the side of the first substrate provided with the film to a second substrate; detachably fixing the second substrate on the upper fixing mechanism, and detachably fixing the side of the first substrate not provided with the film on the lower fixing mechanism; applying, by a force application device, an external force to the upper fixing mechanism and/or the lower fixing mechanism, so that the upper fixing mechanism and the lower fixing mechanism generate therebetween relative movement away from each other; taking one of the external force and time as a variable, and the other as a constant, then counting the number of units whose film is stripped respectively under conditions where the variable is at different values, to obtain a relationship between the number of the units whose film is stripped and the variable.

The method of the embodiment of the present disclosure can accurately evaluate a rule that the film adhesion changes with time or external force. For example, as shown in FIG. 1A, the upper fixing mechanism 11 includes an upper vacuum suction plate, and the lower fixing mechanism 12 includes a lower vacuum suction plate, the upper fixing mechanism 11 suctions the second substrate 32 in a manner of vacuum suctioning, and the lower fixing mechanism 12 suctions the side of the first substrate 31 not provided with the film 33 in the manner of vacuum suctioning.

Figure 3A:
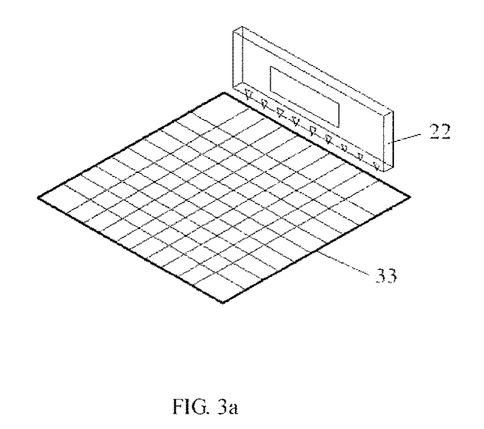
FIG. 3a-FIG. 3b are schematic diagrams of a film being segmented.
Figure 3B:
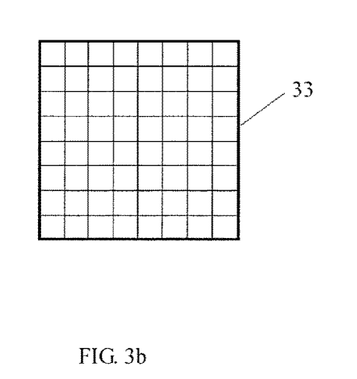

For example, as shown in FIG. 1B, the apparatus further comprises a segmentation machine, which, in the segmenting the film 33, controls the cutter head 22 by using the pressure controller 23 to segment the film 33 on the first substrate 31 into a plurality of units with a constant pressure, as shown in FIG. 3a-FIG. 3b.

Figure 4A:
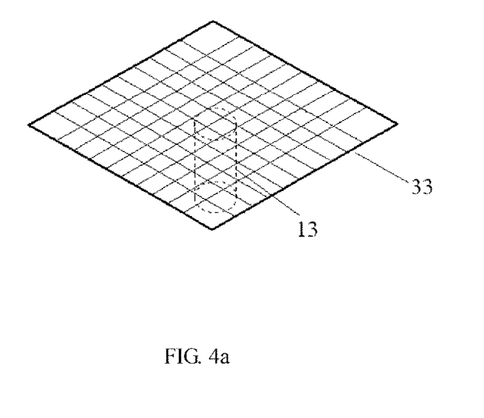
FIG. 4a-FIG. 4b are schematic diagrams of a pull-down mechanism applying a pulling force to the film.
Figure 4B:
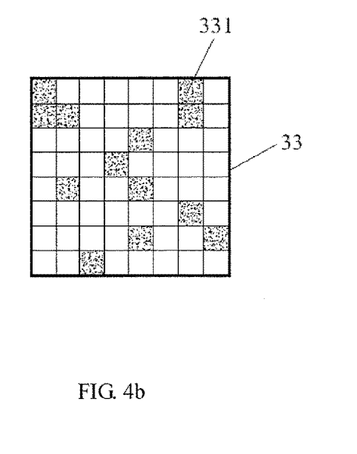

The force application device according to the embodiment of the present disclosure includes a pull-down mechanism 13, and the pull-down mechanism 13 is disposed below the lower fixing mechanism 12 so as to apply a pulling force with a predetermined value to the lower fixing mechanism 12. FIG. 4a-FIG. 4b are schematic diagrams of the pull-down mechanism 13 applying the pulling force to the film; and after the pulling force stops is applied, the status that the film adhesion changes with the time or the pulling force is evaluated by counting the number of the units 331 whose film is stripped.

Further, obtaining of the relationship between the number of the units whose film is stripped and the variable includes: establishing a coordinate system, with a horizontal axis x of the coordinate system as the variable, and avertical axis y as the number of the units whose film is stripped, drawing a plurality of points with coordinate values of $(x_N, y_N)$ in the coordinate system, N being a positive integer; and fitting to obtain an equation of the number of the units whose film is stripped and the variable according to the above coordinate values: $y=k_1x+C_1$, where $k_1$ is a slope, and $C_1$ is a constant.

For example, the fitting method includes a linear regression method and a least square method, etc.

For example, the method may further comprise: taking a second test sample, the second test sample also including a first substrate and a film disposed on the first substrate; segmenting the film into a plurality of units; placing the second test sample after the film is segmented, in a reliability test condition for a predetermined time; attaching the side of the first substrate provided with the film to a second substrate; detachably fixing the second substrate on the upper fixing mechanism, and detachably fixing the side of the first substrate not provided with the film on the lower fixing mechanism; applying, by the force application device, an external force with a predetermined value to the upper fixing mechanism and/or the lower fixing mechanism, so that the upper fixing mechanism and the lower fixing mechanism generate therebetween relative movement away from each other; taking one of the external force and time as a variable, and the other as a constant, then counting the number of units whose film is stripped under conditions where the variable is of different values, to obtain an equation of the number of the units whose film is stripped and the variable under the reliability test condition: $y=k_2x+C_2$, where $k_2$ is a slope, and $C_2$ is a constant; calculating a speed of change of the film adhesion before and after environmental change, according to a formula $\Delta=[(k_2-k_1)/k_1]*100\%$, and determining that the sample has no reliability risk when $\Delta$ is less than or equal to a predetermined percentage.

In the embodiment of the present disclosure, the reliability test condition, for example, refers to a relatively harsh environment, for example, including any one or more conditions of temperature greater than 120° C., humidity greater than 95%, and pressure greater than 0.1 MPa, and predetermined time period greater than 12 hours.

As a first implementation mode of the present disclosure, for example, with the time as a constant, and the pulling force as a variable, the number of the units whose film is stripped under different pulling force conditions is counted, to obtain a relationship between the number of the units whose film is stripped and the pulling force.

Firstly, the cutter head 22, without being applied with a press force, descends directly until it is in contact with the film 33, at this time, a press force is applied onto the cutter head 22 and increased to a predetermined value by the pressure controller 23, and then the cutter head 22 starts cutting the film 33 laterally and longitudinally, and finally divides the film 33 into a plurality of units, as shown in FIG. 3b.

Then, the time for pulling down is set to a constant by the timer 14, and different pulling forces are applied by adding the balancing weights 131 of different weights; when the time for pulling down reaches a predetermined value, the upper vacuum suction plate and the lower vacuum suction plate stop functioning, and at this time, part of the units in the film 33 will be stripped away from the first substrate 31, as shown in FIG. 4b.

Figure 5:
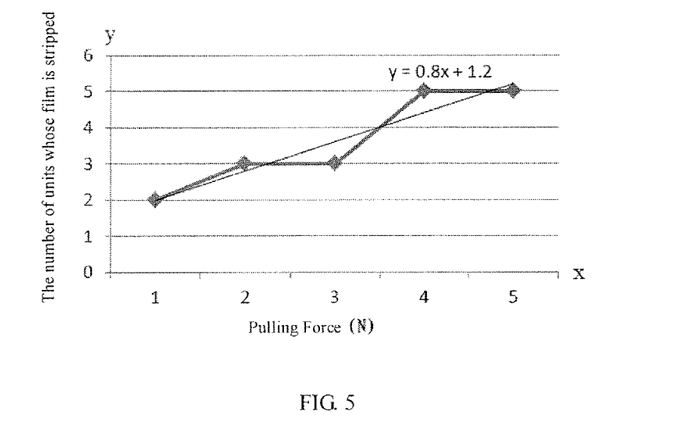
FIG. 5 is a curve chart of relationship between the number of units whose film is stripped and the pulling force.

Thereafter, the relationship between the number of the units whose film is stripped and the pulling force is obtained, by counting the number of the units 331 whose film is stripped. For example, a coordinate system is established, with a horizontal axis x of the coordinate system as the pulling force (N), and a vertical axis y as the number of the units whose film is stripped, a plurality of points with coordinate values of $(x_N, y_N)$ are drawn/plotted in the coordinate system, N being a positive integer; and an equation of the number of the units whose film is stripped and the pulling force is obtained by fitting according to the above coordinate values: $y=k_1 x+C_1$, where $k_1$ is a slope, and $C_1$ is a constant. For example, in FIG. 5, by fitting, $k_1$ is 0.8, and $C_1$ is 1.2. This curve chart can effectively evaluate the status that the film adhesion changes with the external force, which helps to improve the process of evaluating a material of the film and analyze influence of a process change on the film adhesion.

Figure 6:
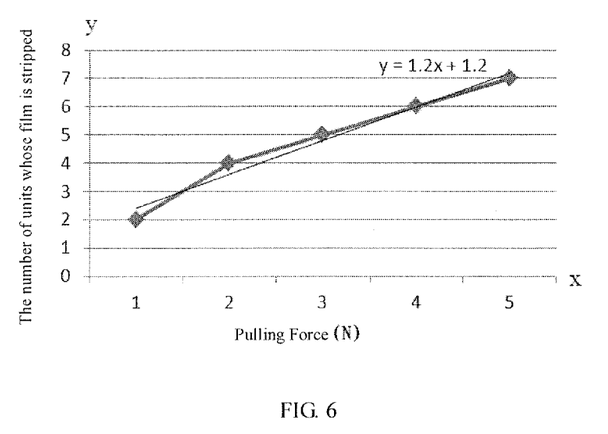
FIG. 6 is a curve chart of the relationship between the number of the units whose film is stripped and the pulling force under a reliability test condition.

Thereafter, the method may further comprise: taking another sample, the sample also including a first substrate 31 and a film 33 disposed on the first substrate 31; processing the film 33 by segmenting; placing the processed sample in a reliability test condition for a predetermined time, repeating the above steps, to obtain an equation of the number of the units whose film is stripped and the pulling force under the reliability test condition: $y=K_2 x+C_2$, where $k_2$ is a slope, and $C_2$ is a constant. For example, in FIG. 6, by fitting, $k_2$ is 1.2, and $C_2$ is 1.2.

As described above, the reliability test condition refers to a relatively harsh environment, for example, including any one or more conditions of temperature greater than 120° C., humidity greater than 95%, and pressure greater than 0.1 MPa, and the predetermined time period greater than 12 hours.

Finally, a product reliability risk is evaluated. When a customer's product is more sensitive to the external force, changes of $k_1$ and $k_2$ before and after the environmental change under a condition of the same time and different pulling forces can be calculated. According to a formula $\Delta=[(k_2-K_1)/k_1]*100\%$, a speed of change of the film adhesion before and after the environmental change is calculated; when $\Delta$ is less than or equal to the predetermined percentage, the product has no reliability risk, otherwise there is a greater reliability risk.

As a second implementation mode of the present disclosure, for example, with the pulling force as a constant, and the time as a variable, the number of the units whose film is stripped under different time conditions is counted, to a obtain a relationship between the number of the units whose film is stripped and the time.

Firstly, the cutter head 22, without being applied with a press force, descends directly until it in contact with the film 33, at this time, a press force is applied onto the cutter head 22 and increased to a predetermined value by the pressure controller 23, and then the cutter head 22 starts cutting the film 33 laterally and longitudinally, and finally divides the film 33 into a plurality of units with an equal size, as shown in FIG. 3b.

Then, the weight of the balancing weights 131 is fixed, and different time periods for pulling down are set by the timer 14; when the pulling force is applied for a specific time period for pulling down, the upper vacuum suction plate and the lower vacuum suction plate stop functioning, and at this time, part of the units in the film 33 will be stripped away from the first substrate 31, as shown in FIG. 4b.

Figure 7:
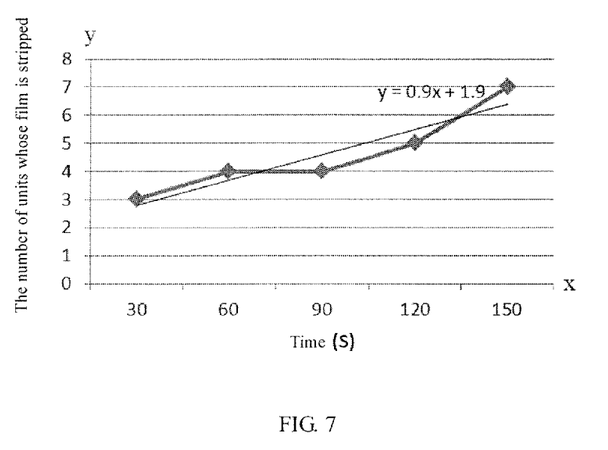
FIG. 7 is a curve chart of relationship between the number of the units whose film is stripped and time.

The test is performed repeatedly for a plurality of time periods for pulling down, and the relationship between the number of the units whose film is stripped and the time is obtained, by counting the number of the units 331 whose film is stripped. For example, a coordinate system is established, with a horizontal axis x of the coordinate system as the time (s), and a vertical axis y as the number of the units whose film is stripped, a plurality of points with coordinate values of $(x_N, y_N)$ are drawn/plotted in the coordinate system, N being a positive integer; and an equation of the number of the units whose film is stripped and the time is obtained by fitting according to the above coordinate values: $y=k_1' x+C_1'$, where $k_1'$ is a slope, and $C_1'$ is a constant. For example, in FIG. 7, by fitting, $k_1'$ is 0.9, and $C_1'$ is 1.9. This curve chart can effectively evaluate the status that the film adhesion changes with the time, which helps to improve the process of evaluating a material of the film and analyze influence of a process change on the film adhesion.

Figure 8:
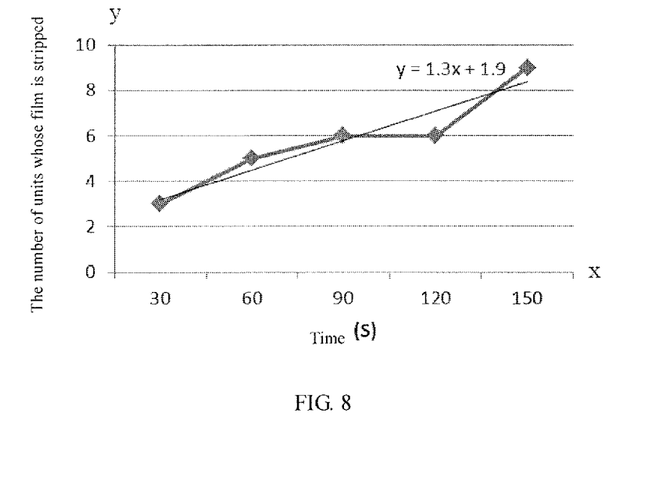
FIG. 8 is a curve chart of the relationship between the number of the units whose film is stripped and the time under a reliability test condition.

Thereafter, the method further comprises: taking another sample, the sample also including a first substrate 31 and a film 33 disposed on the first substrate 31; processing the film 33 by segmenting; placing the processed sample in a reliability test condition for a predetermined time period, repeating the above steps, to obtain the equation of the number of the units whose film is stripped and the time under the reliability test condition: $y=k_2' x+C_2'$, where $k_2'$ is a slope, and $C_2'$ is a constant. For example, in FIG. 8, by fitting, $k_2'$ is 1.3, and $C_2'$ is 1.9.

As described above, the reliability test condition refers to a relatively harsh environment, for example, including any one or more conditions of temperature greater than 120° C., humidity greater than 95%, and pressure greater than 0.1 MPa, and predetermined time period greater than 12 hours.

Finally, a product reliability risk is evaluated. When a customer's product is more sensitive to the time, changes of $k_1'$ and $k_2'$ before and after the environmental change under a condition of the same pulling force and different times can be calculated. According to a formula $\Delta'=[(k_2'-k_1')/k_1']*100\%$, a speed of change of the film adhesion before and after the environmental change is calculated; when $\Delta'$ is less than or equal to the predetermined percentage, the product has no reliability risk, otherwise there is a greater reliability risk.

As a third implementation mode of the present disclosure, respective steps in the first embodiment and the second embodiment are completed at the same time, $\Delta$ and $\Delta'$ are evaluated together, and the status that the film adhesion changes before and after the environmental change is evaluated; when $\Delta$ and $\Delta'$ are respectively less than or equal to the predetermined percentage, the reliability risk of the product is minimized.

As compared with the conventional technology, the method provided by the embodiment of the present disclosure has beneficial effects as follows: the embodiment evaluates by means of a single product of the sample (e.g., the color filter substrate), which reduces the waste of resources and materials, and can predict in advance and avoid a product quality risk; it can segment the film by a constant force, and form a plurality of units with an equal segmentation area for evaluation, so that an evaluation result is more accurate and reliable; It can establish a curve that the film adhesion changes with time or external force, so as to evaluate the status of the film adhesion more accurately; it can effectively evaluate the status that the film adhesion changes before and after the environmental change, so as to evaluate the risk of occurrence of the undesirable phenomenon to the product in the reliability test.

The foregoing embodiments merely are exemplary embodiments of the disclosure, and not intended to define the scope of the disclosure, and the scope of the disclosure is determined by the appended claims.

The present application claims priority of Chinese Patent Application No. 201510130546.3 filed on Mar. 24, 2015, the disclosure of which is incorporated herein by reference in its entirety as part of the present application.

What is claimed is:

1. An apparatus for evaluating film adhesion, the film being disposed on a first substrate, a side of the first substrate provided with the film being attached to a second substrate, and the film being divided into a plurality of units, wherein
the apparatus comprises an evaluation machine, the evaluation machine including an upper fixing mechanism and a lower fixing mechanism disposed opposite to each other, the second substrate being detachably fixed on the upper fixing mechanism, and a side of the first substrate not provided with the film being detachably fixed on the lower fixing mechanism;
the evaluation machine further includes a force application device, the force application device being configured to apply an external force to the upper fixing mechanism and/or the lower fixing mechanism, so that the upper fixing mechanism and the lower fixing mechanism generate therebetween relative movement away from each other; and
the apparatus further comprises a calculating module, and the calculating module is configured for:
establishing a coordinate system, with a horizontal axis x of the coordinate system as external force or time, and a vertical axis y as a number of units whose film is stripped;
drawing a plurality of points with coordinate values of $(x_N, y_N)$ in the coordinate system, N being a positive integer; and
fitting to obtain an equation of x and y according to the above coordinate values: $y=kx+C$, where k is a slope, and C is a constant.

2. The apparatus according to claim 1, wherein the force application device includes a pull-down mechanism, the pull-down mechanism being disposed below the lower fixing mechanism, so as to apply a pulling force to the lower fixing mechanism.

3. The apparatus according to claim 2, wherein the pull-down mechanism includes at least one balancing weight detachably disposed below the lower fixing mechanism.

4. The apparatus according to claim 1, wherein the upper fixing mechanism includes an upper vacuum suction plate, and the lower fixing mechanism includes a lower vacuum suction plate.

5. The apparatus according to claim 1, further comprising a segmentation machine, the segmentation machine including a stage, a cutter head disposed above the stage, and a pressure controller configured for controlling a cutting pressure of the cutter head, the stage being configured for placing the first substrate, the side of the first substrate provided with the film being disposed toward the cutter head, and the segmentation machine being configured for segmenting the film into a plurality of units.

6. The apparatus according to claim 5, wherein a side of the cutter head toward the stage is provided with a plurality of blades uniformly spaced, the cutter head is able to move relative to the stage, and the cutter head is able to rotate around an installation shaft for installing the cutter head.

7. The apparatus according to claim 1, wherein the evaluation machine is further provided with a timer, the timer being configured for setting time for the force application device to apply a pulling force.

8. The apparatus according to claim 1, wherein the side of the first substrate provided with the film is attached to the second substrate by transparent adhesive.

9. The apparatus according to claim 1, wherein the film is a color filter layer.

10. The apparatus according to claim 1, further comprising a determining module, the determining module being configured for determining whether a sample under test has a reliability risk or not, according to a difference of k values obtained respectively under a normal condition and a reliability test condition.

11. A method for evaluating film adhesion, comprising:
taking a first test sample, the first test sample including a first substrate and a film disposed on the first substrate;
segmenting the film into a plurality of units;
attaching a side of the first substrate provided with the film to a second substrate;
detachably fixing the second substrate on an upper fixing mechanism, and detachably fixing a side of the first substrate not provided with the film on a lower fixing mechanism;
applying an external force with a predetermined value to the upper fixing mechanism and/or the lower fixing mechanism, so that the upper fixing mechanism and the lower fixing mechanism generate therebetween relative movement away from each other; and
taking one of the external force and time as a variable, and the other as a constant, then counting the number of units whose film is stripped respectively under conditions where the variable is of different values, to obtain a relationship between the number of the units whose film is stripped and the variable,
wherein obtaining of a relationship between the number of the units whose film is stripped and the variable includes:
establishing a coordinate system, with a horizontal axis x of the coordinate system as the variable, and a vertical axis y as the number of the units whose film is stripped, drawing a plurality of points with coordinate values of $(x_N, y_N)$ in the coordinate system, N being a positive integer;
fitting to obtain an equation of the number of the units whose film is stripped and the variable according to the above coordinate values: $y=k_1 x+C_1$, where $k_1$ is a slope, and $C_1$ is a constant.

12. The method according to claim 11, wherein the external force refers to a pulling force that is applied to the lower fixing mechanism.

13. The method according to claim 11, further comprising:
taking a second test sample, the second test sample including a third substrate and a second film disposed on the third substrate;
segmenting the second film into a plurality of units;
placing the second test sample after the second film is segmented, in a reliability test condition for a predetermined time;
attaching a side of the third substrate provided with the second film to a fourth substrate;
detachably fixing the fourth substrate on the upper fixing mechanism, and detachably fixing a side of the third substrate not provided with the second film on the lower fixing mechanism;
applying an external force with a predetermined value to the upper fixing mechanism and/or the lower fixing mechanism, so that the upper fixing mechanism and the lower fixing mechanism generate therebetween relative movement away from each other;
taking one of the external force and time as a variable, and the other as a constant, then counting the number of units whose film is stripped under conditions where the variable is of different values, to obtain an equation of the number of the units whose film is stripped and the variable under the reliability test condition: $y=k_2x+C_2$, where $k_2$ is a slope, and $C_2$ is a constant;

calculating a speed of change of the film adhesion before and after environmental change, according to a formula $\Delta=[(k_2-k_1)/k_1]*100\%$, and determining that the sample has no reliability risk, when $\Delta$ is less than or equal to a predetermined percentage.

14. The method according to claim 13, wherein the reliability test condition includes any one or more conditions of temperature greater than 120° C., humidity greater than 95%, and pressure greater than 0.1 MPa, and the predetermined time being greater than 12 hours.

15. The method according to claim 11, wherein during segmenting the film into a plurality of units, the film is segmented into a plurality of units with a constant pressure.

16. The method according to claim 11, wherein, with the time as a constant, and the pulling force as a variable, the number of the units whose film is stripped respectively under different pulling force conditions is counted, and a relationship between the number of the units whose film is stripped and the pulling force is obtained.

17. The method according to claim 11, wherein, with the pulling force as a constant, and the time as a variable, the number of the units whose film is stripped respectively under different time conditions is counted, and a relationship between the number of the units whose film is stripped and the time is obtained.

* * * * *